(12) United States Patent
Steiner et al.

(10) Patent No.: US 7,464,706 B2
(45) Date of Patent: Dec. 16, 2008

(54) UNIT DOSE CARTRIDGE AND DRY POWDER INHALER

(75) Inventors: Solomon S. Steiner, Mount Kisco, NY (US); Trent A. Poole, South Amherst, MA (US); Per B. Fog, Bedford Hills, NY (US); Roderike Pohl, Sherman, CT (US); Michael Crick, Middlebury, CT (US); Robert Feldstein, Yonkers, NY (US)

(73) Assignee: MannKind Corporation, Valencia, CA (US)

( * ) Notice: Subject to any disclaimer, the term of this patent is extended or adjusted under 35 U.S.C. 154(b) by 954 days.

(21) Appl. No.: 10/655,153

(22) Filed: Sep. 4, 2003

(65) Prior Publication Data

US 2004/0182387 A1   Sep. 23, 2004

Related U.S. Application Data

(63) Continuation-in-part of application No. 09/621,092, filed on Jul. 21, 2000, now Pat. No. 7,305,986.

(60) Provisional application No. 60/206,123, filed on May 22, 2000, provisional application No. 60/145,464, filed on Jul. 23, 1999.

(51) Int. Cl.
    *A61M 11/00* (2006.01)
(52) U.S. Cl. ............... 128/203.15; 128/203.12
(58) Field of Classification Search ............ 128/203.15, 128/203.21, 200.12, 200.24, 203.12
    See application file for complete search history.

(56) References Cited

U.S. PATENT DOCUMENTS

| | | | |
|---|---|---|---|
| 2,549,303 A | 4/1951 | Friden | |
| 3,669,113 A | 6/1972 | Altounyan et al. | |
| 3,823,816 A | 7/1974 | Controullis et al. | |
| 3,823,843 A | 7/1974 | Stephens et al. | |
| 3,906,950 A | 9/1975 | Cocozza | |
| 3,921,637 A | 11/1975 | Bennie et al. | |
| 4,040,536 A | 8/1977 | Schwarz | |
| 4,047,525 A | 9/1977 | Kulessa et al. | |
| 4,148,308 A | 4/1979 | Sayer | |
| 4,268,460 A * | 5/1981 | Boiarski et al. | ............ 261/1 |
| 4,275,820 A | 6/1981 | LeBlond | |
| 4,407,525 A | 10/1983 | Hoppe | |
| 4,487,327 A | 12/1984 | Grayson | |
| 4,524,769 A | 6/1985 | Wetterlin | |
| 4,534,345 A | 8/1985 | Wetterlin | |
| 4,592,348 A | 6/1986 | Waters, IV et al. | |
| 4,792,451 A | 12/1988 | Kim | |

(Continued)

FOREIGN PATENT DOCUMENTS

DE   36 39 836   6/1988

(Continued)

*Primary Examiner*—Steven O Douglas
(74) *Attorney, Agent, or Firm*—Louis C. Cullman; Michelle S. Glasky; K&L Gates LLP

(57) ABSTRACT

A dry powder inhaler having improved aerodynamic properties for diluting, dispersing, and metering drug particles for increasing the efficiency of pulmonary drug delivery to a patient is described. The inhaler comprises, in general, a housing having an air intake, an air flow-control/check-valve, a mixing section and a mouthpiece. A cartridge loaded with a single dose of medicament can be installed in the mixing section.

36 Claims, 15 Drawing Sheets

U.S. PATENT DOCUMENTS

| | | | |
|---|---|---|---|
| 4,841,964 A | 6/1989 | Hurka et al. | |
| 4,907,583 A | 3/1990 | Wetterlin et al. | |
| 4,926,852 A | 5/1990 | Zoltan et al. | |
| 4,991,605 A | 2/1991 | Keritsis | |
| 5,027,806 A | 7/1991 | Zoltan et al. | |
| 5,067,500 A | 11/1991 | Keritsis | |
| 5,152,284 A | 10/1992 | Valentini et al. | |
| 5,170,801 A | 12/1992 | Casper et al. | |
| 5,239,992 A | 8/1993 | Bougamont et al. | |
| 5,301,666 A | 4/1994 | Lerk et al. | |
| 5,327,883 A | 7/1994 | Williams et al. | |
| 5,328,464 A | 7/1994 | Kriesel et al. | |
| 5,404,871 A | 4/1995 | Goodman et al. | |
| 5,476,093 A | 12/1995 | Lankinen | |
| 5,483,954 A | 1/1996 | Mecikalski | |
| 5,487,378 A | 1/1996 | Robertson et al. | |
| 5,492,112 A | 2/1996 | Mecikalski et al. | |
| 5,505,194 A | 4/1996 | Adjei et al. | |
| 5,524,613 A | 6/1996 | Haber et al. | |
| 5,542,411 A | 8/1996 | Rex | |
| 5,562,918 A | 10/1996 | Stimpson | |
| 5,577,497 A | 11/1996 | Mecikalski et al. | |
| 5,622,166 A | 4/1997 | Eisele et al. | |
| 5,632,971 A | 5/1997 | Yang | |
| 5,645,051 A | 7/1997 | Schultz et al. | |
| 5,655,523 A | 8/1997 | Hodson et al. | |
| 5,687,710 A | 11/1997 | Ambrosio et al. | |
| 5,699,789 A | 12/1997 | Hendricks | |
| 5,714,007 A | 2/1998 | Pletcher et al. | |
| 5,727,546 A | 3/1998 | Clarke et al. | |
| 5,740,794 A | 4/1998 | Smith et al. | |
| 5,746,197 A * | 5/1998 | Williams | 128/200.23 |
| 5,758,638 A | 6/1998 | Kreamer | |
| 5,775,320 A | 7/1998 | Patton et al. | |
| 5,785,049 A | 7/1998 | Smith et al. | |
| 5,797,391 A | 8/1998 | Cook et al. | |
| 5,813,397 A | 9/1998 | Goodman et al. | |
| 5,881,719 A * | 3/1999 | Gottenauer et al. | 128/203.15 |
| 5,884,620 A | 3/1999 | Gonda et al. | |
| 5,896,855 A | 4/1999 | Hobbs et al. | |
| 5,901,703 A | 5/1999 | Ohki et al. | |
| 5,921,237 A | 7/1999 | Eisele et al. | |
| 5,983,893 A | 11/1999 | Wetterlin | |
| 6,006,747 A | 12/1999 | Eisele et al. | |
| 6,029,663 A | 2/2000 | Eisele et al. | |
| 6,055,980 A | 5/2000 | Mecikalski et al. | |
| 6,073,629 A | 6/2000 | Hardy et al. | |
| 6,109,261 A | 8/2000 | Clarke et al. | |
| 6,116,237 A | 9/2000 | Schultz et al. | |
| 6,116,238 A | 9/2000 | Jackson et al. | |
| 6,116,239 A | 9/2000 | Volgyesi | |
| 6,273,085 B1 | 8/2001 | Eisele et al. | |
| 6,273,086 B1 * | 8/2001 | Ohki et al. | 128/203.21 |
| 6,328,034 B1 | 12/2001 | Eisele et al. | |
| 6,347,629 B1 | 2/2002 | Braithwaite | |
| 6,363,932 B1 | 4/2002 | Forchione et al. | |
| 6,394,085 B1 | 5/2002 | Hardy et al. | |
| 6,418,926 B1 | 7/2002 | Chawla | |
| 6,427,688 B1 | 8/2002 | Ligotke et al. | |
| 6,543,448 B1 | 4/2003 | Burr et al. | |
| 6,546,929 B2 | 4/2003 | Burr et al. | |
| 6,561,186 B2 | 5/2003 | Casper et al. | |
| 6,575,160 B1 | 6/2003 | Volgyesi | |
| 6,578,571 B1 * | 6/2003 | Watt | 128/200.14 |
| 6,606,992 B1 | 8/2003 | Schuler et al. | |
| 6,644,309 B2 | 11/2003 | Casper et al. | |
| 6,655,379 B2 | 12/2003 | Clark et al. | |
| 6,655,381 B2 | 12/2003 | Keane et al. | |
| 6,681,767 B1 | 1/2004 | Patton et al. | |

FOREIGN PATENT DOCUMENTS

| | | |
|---|---|---|
| DE | 195 19 840 | 12/1996 |
| EP | 0 143 524 | 6/1985 |
| EP | 0 180 543 | 5/1986 |
| EP | 0 308 637 | 3/1989 |
| EP | 0 388 621 | 9/1990 |
| EP | 0 581 473 | 2/1994 |
| EP | 0 640 354 | 1/1995 |
| EP | 0 666 085 | 8/1995 |
| EP | 0 844 007 | 5/1998 |
| GB | 0 716 815 | 10/1954 |
| GB | 2 072 536 | 10/1981 |
| GB | 2 148 841 | 6/1985 |
| GB | 2 253 200 | 9/1992 |
| GB | 2 262 452 | 6/1993 |
| WO | WO 91/19524 | 12/1991 |
| WO | WO 92/08509 | 5/1992 |
| WO | WO 94/19041 | 9/1994 |
| WO | WO 95/05208 | 2/1995 |
| WO | WO 96/22802 | 8/1996 |
| WO | WO 97/01365 | 1/1997 |
| WO | WO 98/26827 | 6/1998 |
| WO | WO 98/41255 | 9/1998 |
| WO | WO 01/07107 | 2/2001 |
| WO | WO 01/66064 | 9/2001 |
| WO | WO 03/05547 | 7/2003 |
| WO | WO 03/055547 | 7/2003 |

* cited by examiner

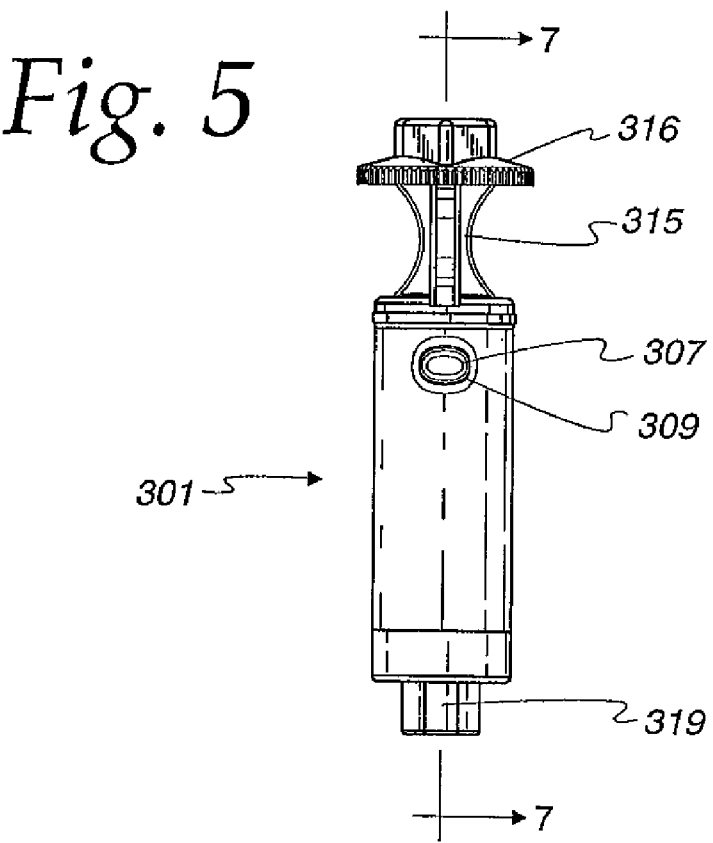
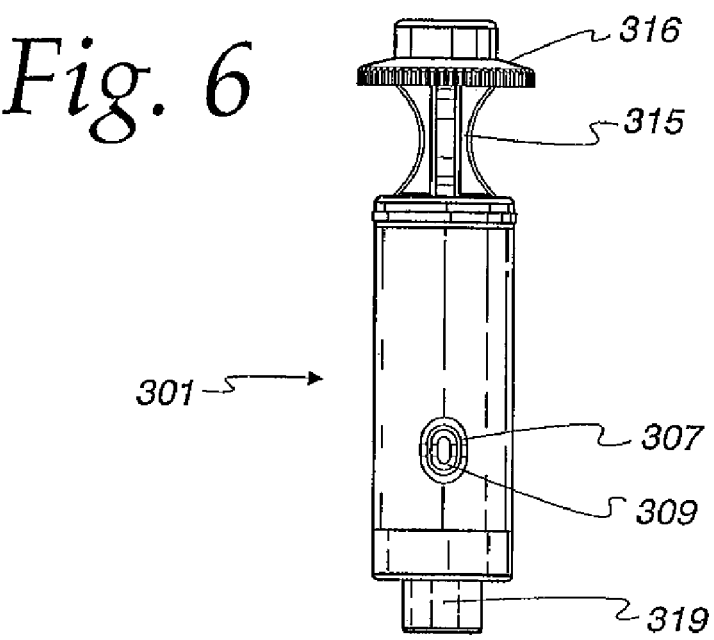

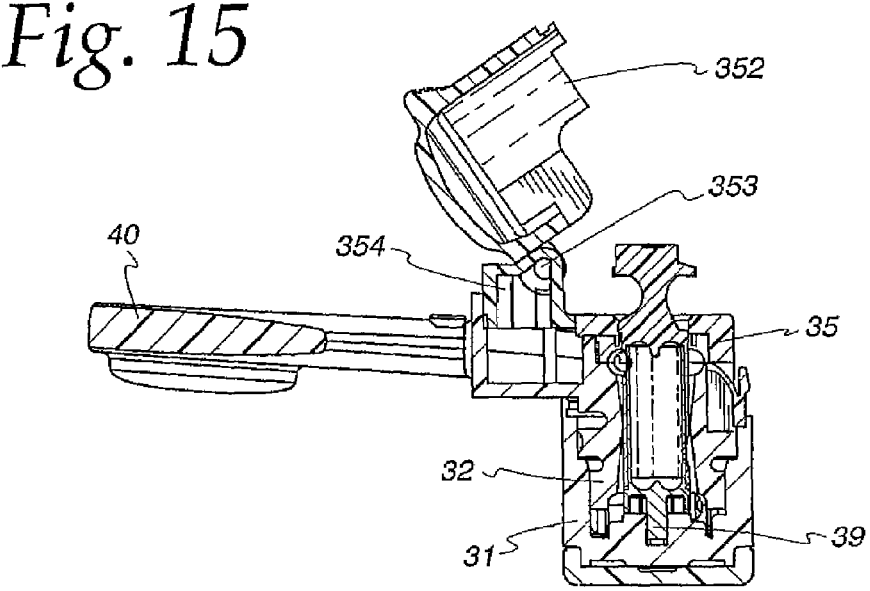
Fig. 15
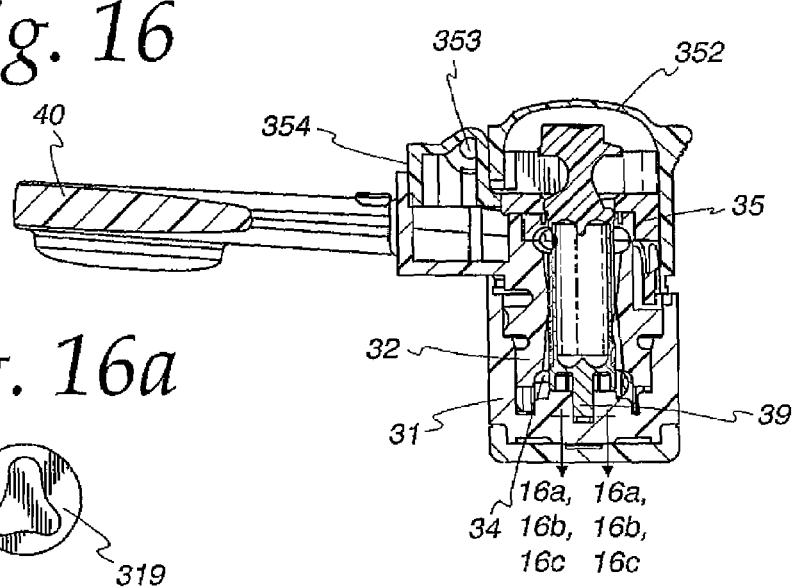
Fig. 16
Fig. 16a
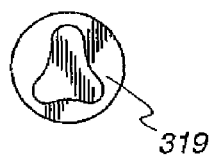
Fig. 16b
Fig. 16c
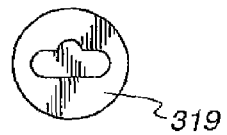

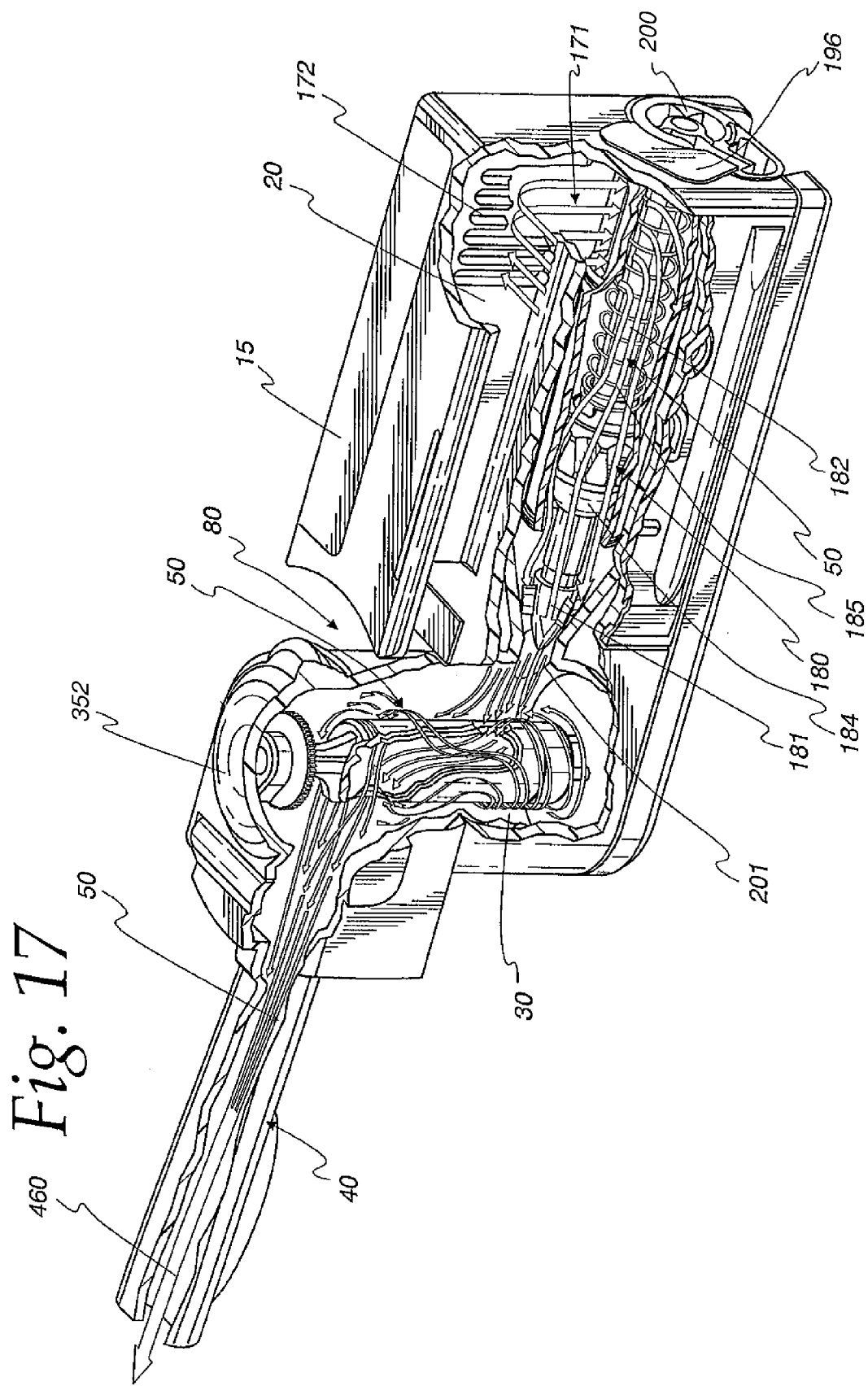

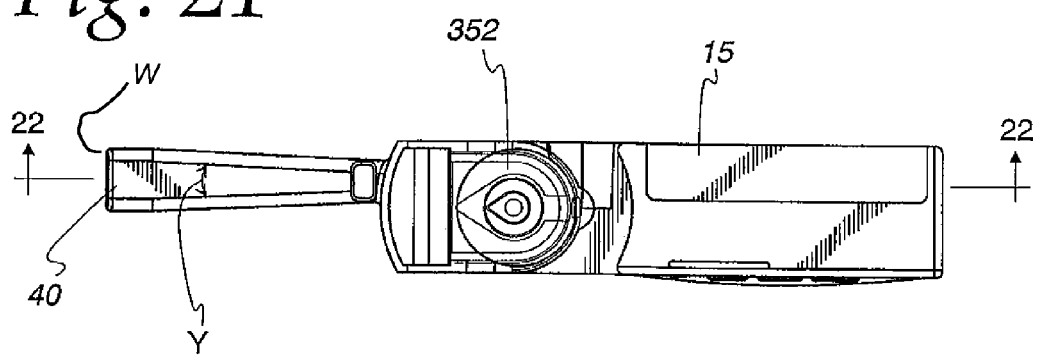
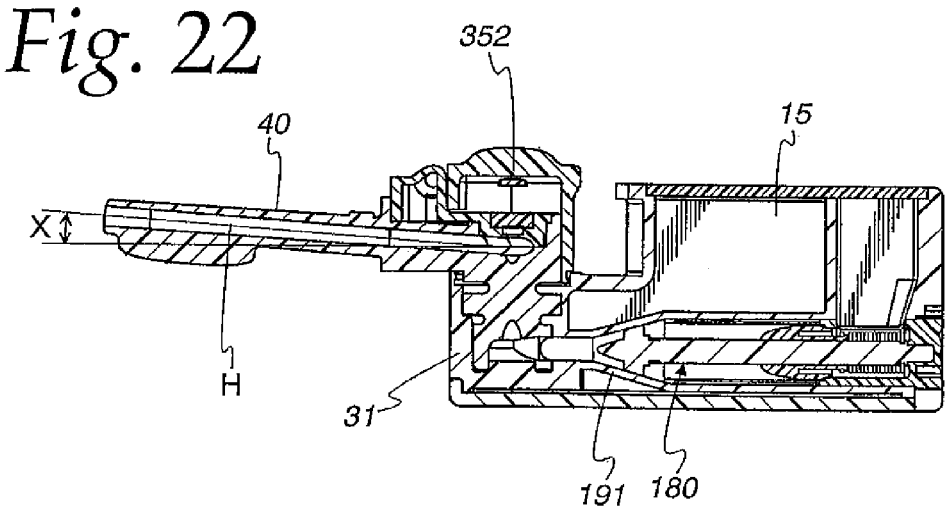

UNIT DOSE CARTRIDGE AND DRY POWDER INHALER

This application is a Continuation-in-Part of U.S. utility patent application Ser. No. 09/621,092, filed 21 Jul. 2000; which application claims domestic priority from U.S. provisional applications U.S. Ser. No. 60/145,464 filed 23 Jul. 1999, entitled Dry Powder Inhaler, and U.S. Ser. No. 60/206,123 filed 22 May 2000, entitled Unit Dose Capsules and Dry Powder Inhaler Device.

FIELD OF THE INVENTION

The present invention is in the field of drug administration inhalers having improved control over system volumetric air flow rate, medicament particle transport, particle dispersion, particle metered dosimetry and patient compliance.

BACKGROUND OF THE INVENTION

In the early 1970's it was found that certain medicines could be administered in dry-powder form directly to the lungs by inhalation through the mouth or inspiration through the nose. This process allows the medicine to bypass the digestive system, and may, in certain cases, allow smaller dosages to be used to achieve the same results as orally ingested or injected medicines. In some cases, it provides a delivery technique that reduces side effects for medicines and interactions with other prescribed medicines, as well as providing a more rapid drug medication uptake.

Inhaler devices typically deliver medicine in a liquid droplet mist or as a dry powder aerosol. Deposition of particulate matter within the human lungs is a very complex and not fully understood phenomenon. People breathe over a relatively broad tidal volume. It is known that lower transport velocities of gas-entrained particles entering the mouth avoid impaction better within the oropharyngeal cavity. This is particularly true of particles greater than one to two microns in diameter.

In order for particles to remain suspended in a gas stream, their superficial transport velocity must be greater than their gravity settling velocity. For example, a 100 micron particle must have a transport gas velocity of approximately 7 ft/sec or greater for the 100 micron particle to remain in a particle/gas entrainment state. The required transport velocity for smaller particles is much less High speed particles have a greater propensity to impact and deposit on the tissue lining of the oropharyngeal cavity, as noted above. Thus, a significant number of particles are lost and will not enter the lungs, if those particles are not transported at the correct velocity.

Another common problem with inhalers is that the particles agglomerate, causing clumping of particles that then adhere to the inhaler or the oral cavity, rather than entering the lungs. Most approaches to this problem have been to include a surfactant in, on or with the particles to decrease the adhesion between particles.

Importantly, it should not be difficult for a patient to load the inhaler with medicine, and to easily and properly use the inhaler so that the correct dosage is actually administered. Many current dry particle inhalers fail in one or more of these important criteria.

It is therefore an object of the present invention to provide inhalers which are easy to properly use, and which deliver drug powders so that the powder enters the lungs instead of adhering to the back of the throat.

It is an object of the invention to provide an inhaler which will operate effectively with dry powder medicaments having particles ranging in size from about 0.5 to about 10 microns, and preferably from about 1 to about 5 microns in size.

It is a further object of the present invention to provide an inhaler that can operate effectively over a broad inhalation tidal volume range of human breath.

It is a still further object of the present invention to provide an inhaler which controls the volume and velocity of air flow so as to provide effective and desirable colimation, de-agglomeration and entrainment of the inhaled drug.

A related object is to provide an inhaler which creates a high-shear air flow field and controlled circulating gas action to break up particle agglomeration during proper inhaler usage.

A more specific object is to provide an inhaler mouthpiece which is sized and shaped to develop an air flow which will air stream entrained medicament particles through the oropharyngeal cavity.

Another specific object is to provide a medicament-containing inhaler cartridge which will supply medicament for complete air entrainment and proper dispersion into the air stream.

Yet another object is to provide an inhaler air-flow-controlling check valve which will straighten the air flow and limit the air flow volume and velocity to values between pre-determined maxima and minima so as to properly entrain, de-agglomerate and deliver medicament particles to the inhaler user.

Other objects and advantages of the invention will become apparent upon reading the following detailed description and upon reference to the drawings. Throughout the drawings, like reference numerals refer to like parts.

SUMMARY OF THE INVENTION

A dry powder inhaler (DPI) includes an air intake and check valve section; a mixing and cartridge section; and a mouthpiece all designed to control the volume and velocity of the inhaled air and aerosolized drug. This inhaler can be operated over a very broad inhalation tidal volume range of human breath. Several features of the inhaler provide advantageous properties, most significantly with respect to using carefully designated aerodynamic forces to dilute and de-agglomerate the medicament particles, rather than using broad high pressure forces that would contribute to relatively great particle losses in the oropharyngeal region.

The inhaler intake chamber mounts a check valve bulb having a tapered bulb, bulb travel rod and biasing spring, and one or more perimeter chutes or venturis on the bulb to modulate and control the flow of air through the device. The intake further optionally includes a feedback module (not shown) to generate a tone indicating to the user when the adequate inhalation air-flow rate has been achieved.

The inhaler mixing section holds a cartridge containing a dry powder medicament. The cartridge has two telescopically assembled halves, and each half has an air inlet hole or orifice-port and an air outlet hole or orifice-port. When the halves are twisted so as to align the air holes, the air stream from the check valve enters the cartridge and then picks up, fluidizes and de-agglomerates the medicament powder in the cartridge. The airflow entraining the particles then exits the cartridge and flows through the mouthpiece to the inhaler user. The cover on the mixing section can open only when the mouthpiece is at an appropriate pre-determined angle to the intake conduit. The mixing section helps to impart a cyclonic flow to air passing through the mixing chamber and cartridge.

An important feature of the inhaler is the mouthpiece. The mouthpiece is integrated to the swivel joint of the mixing section, and can be rotated back into the inhaler intake section and then enclosed by a cover for storage. A mouthpiece transport conduit has the ability to expand the cross-section of the air flow, which in turn reduces the velocity of approach of the drug powder into the oral cavity. As shown in FIGS. 10, 18, 19, 21 and 23, the mouthpiece is offset with respect to the centerline of the mixing cavity and mounted cartridge, and the airflow inlet from the check valve mechanism into the mixing chamber and cartridge is also offset. These tangential offsets encourage a helical airflow around the cartridge, as explained in further detail below. Initially, the tangential mouthpiece exit tube increases the velocity of the transport gas, which in turn inducts the discharged particles into the exit tube. The mouthpiece exit tube then expands in one dimension and the transport gas slows while the particle concentration per unit volume becomes more dilute. Flow is expanded to create a secondary shear flow, which helps to further de-agglomerate particles. This also creates a horizontal aspect ratio and therefore aerosol discharge path that is more effective in negotiating and streaming the aerosol through the convoluted pathway of the oral pharynx.

The mouthpiece expansion wall divergence angle is important for stable particle transport conditions to exist. An optimum divergence angle is between 14 and 16 degrees. However, a slightly larger 17 degree divergence angle can be used to achieve a horizontal aerosol discharge path with a 3:1 aspect ratio closely approximating the aspect ratio at the rear of the human throat. Once the expansion divergence has reached a specified limit, the continuing slot discharge tube maintains the proper collimation of the particles for controlled particle injection speed and direction of the path of the particles into the oral cavity. The mouthpiece includes a tongue depressor, and a tactile protrusion to contact the lips of the user to tell the user that the Dry Powder Inhaler (DPI) is in the correct position.

The cartridge halves can be twisted into and out of positions in which the air inlet holes and the air outlet holes are respectively aligned. The cartridge can only be inserted into the mixing chamber when a cartridge alignment boss is aligned with a receiving recess at the bottom of the mixing chamber, and a cartridge collar and engages a mating mixing chamber collar (FIG. 2). Each cartridge has a unique key on each half that fits only with a particular part of the inhaler, thereby insuring that the proper cartridge containing the proper medicament is preselected, and further insuring that the cartridge is installed properly in the inhaler.

BRIEF DESCRIPTION OF THE DRAWINGS

FIG. 3, including

FIG. 4, including

FIG. 5 is a front elevational view of the cartridge shown in FIGS. 3 and 4.

FIG. 6 is a rear elevational view of the cartridge shown in FIGS. 3, 4 and 5.

FIG. 15 is a sectional view taken substantially in the plane of line 15-15 in FIG. 13.

FIG. 16 is a sectional view taken substantially in the plane of line 16-16 in FIG. 14.

FIGS. 16a, 16b and 16c are fragmentary sectional views taken substantially in the plain of line 16a-16c in FIG. 16.

FIG. 17 is an isometric view showing the inhaler of FIGS. 1 and 2, parts being broken away to permit the diagramming of air flow through the inhaler.

FIG. 21 is a top plan view of the inhaler shown in FIG. 20.

FIG. 22 is a sectional view taken substantially in the plane of line 22-22 in FIG. 21.

While the invention will be described in connection with several preferred embodiments and procedures, it will be understood that it is not intended to limit the invention to these embodiments and procedures. On the contrary, it is intended to cover all alternatives, modifications and equivalents as may be included within the spirit and scope of the invention as defined by the appended claims.

DETAILED DESCRIPTION OF THE INVENTION

An improved inhaler has been developed which has several novel features optimizing performance. Medicament particles can be delivered/administered over a broad range of inhalation velocity and tidal volume of human breath. An inhaler mouthpiece exit tube dilutes, expands, and collimates the particle dispersoid so that the particles do not re-agglomerate during delivery. This inhaler provides the means to effect a process whereby particles are fluidized, suspended, then scavenged from the walls by re-circulating scrubbing air, as well as higher speed-flow-through air, followed by a high-shear flow field discharge into an expanded, slower-moving mass of air that disperses and meters the particle concentration expelled from the unit dose cartridge upper outlet port.

Inhaler Overview

Figure 1:
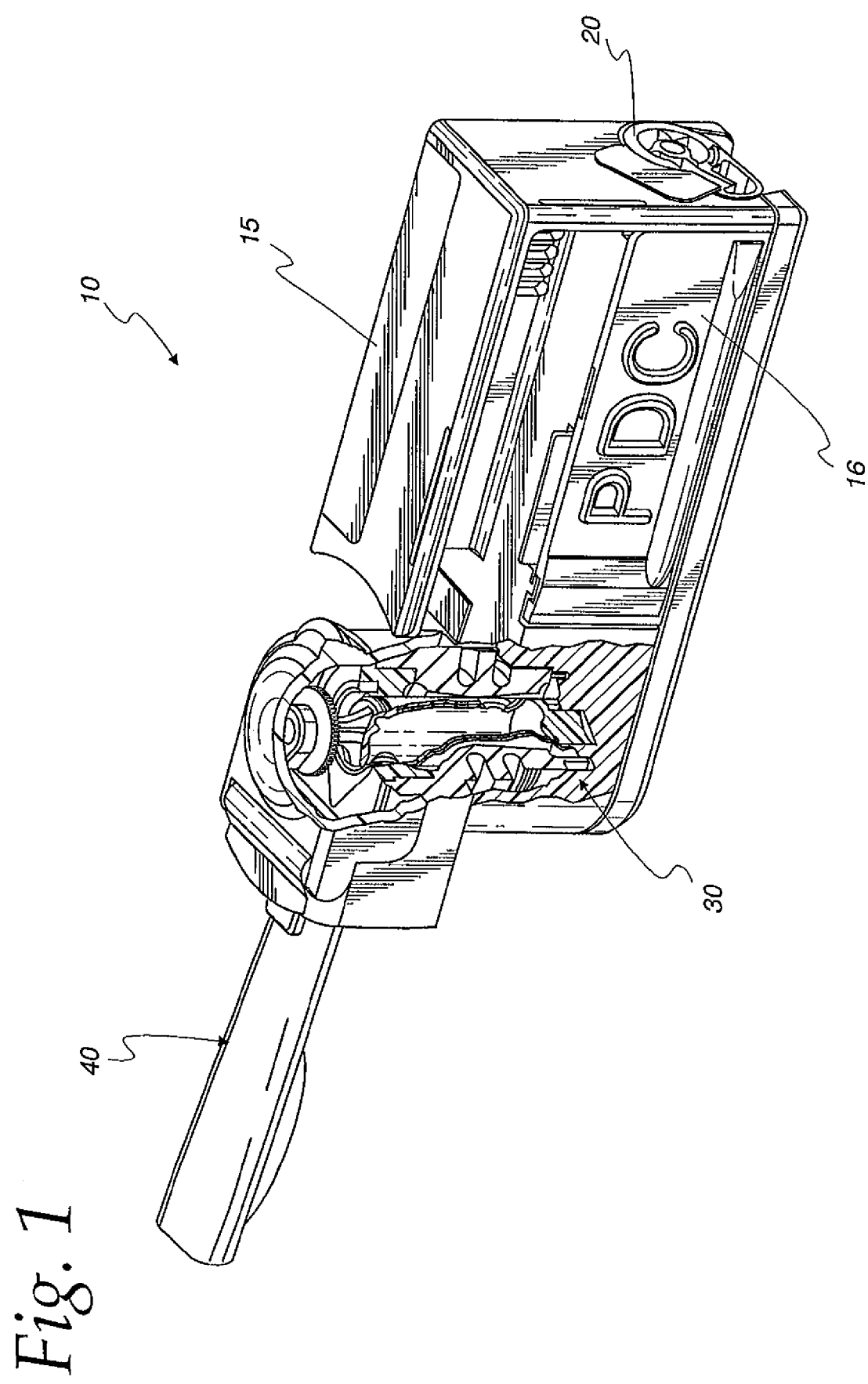
FIG. 1 is an isometric view of the inhaler embodying the invention.

FIG. 1 shows an embodiment of a dry powder inhaler 10 described and claimed herein. In broad conceptual terms, an inhaler housing 15 includes an intake section 20, a mixing section 30 and a mouthpiece 40. In the preferred embodiment, this inhaler housing 15 is approximately 93 mm long, 38 mm high, and 22 mm thick. The other parts illustrated and described here are of proportionate size. The mouthpiece 40 can be swiveled from a stored position within the housing 15 to a cartridge installation position in which the mouthpiece 40 is oriented at 90 degrees to the long dimension of the housing. When a cap 352 is closed, the mouthpiece can then be further rotated into an operating position in which the mouthpiece is located at a 180 degree position to the long dimension of the housing. When the mouthpiece 40 is stored within the inhaler 15, a sliding dirt shield cover 16 slidably mounted stored on the housing can be slid upwardly to protect the mouthpiece 40 and the air intake conduit entrance of the inhaler. The housing 15 can be formed of a gamma radiation-proof polycarbonate plastic for the rapid sterilization of the inhaler in mass production, as well as in clinical-hospital use.

Figure 2:
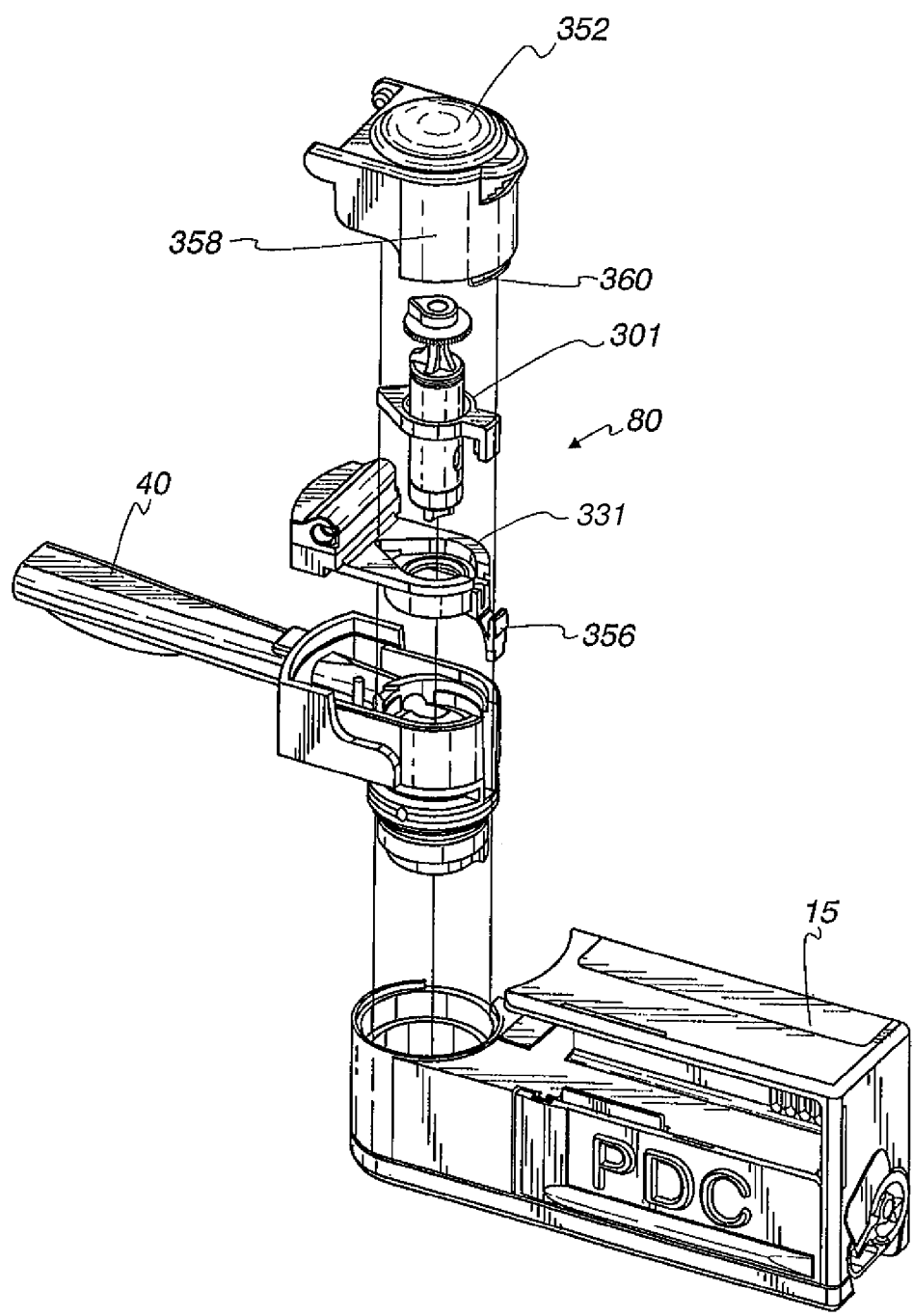
FIG. 2 is an exploded view of the inhaler shown in FIG. 1.
Figure 3A:
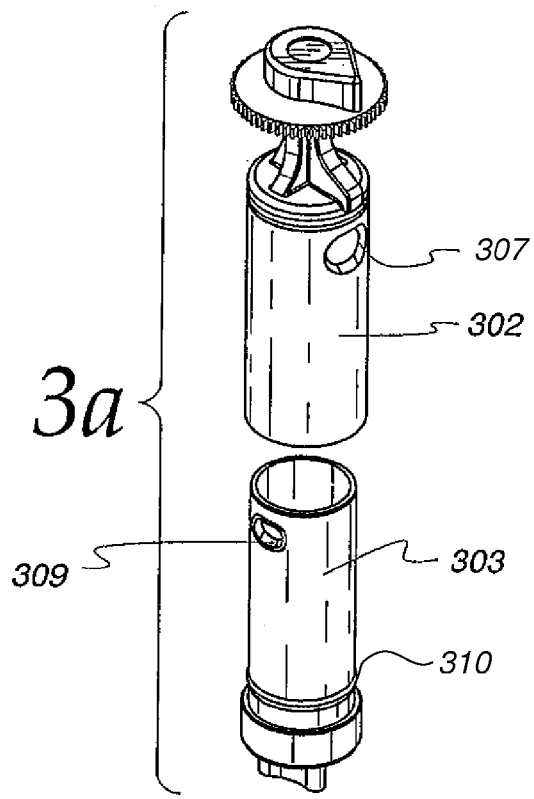
FIGS. 3a, 3b and 3c, is a front isometric view of the medicament containing cartridge used with the inhaler, showing cartridge outlet hole or orifice port alignments.
Figure 3B:
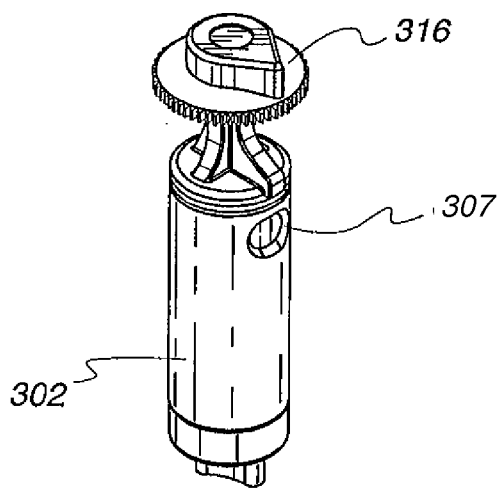
Figure 3C:
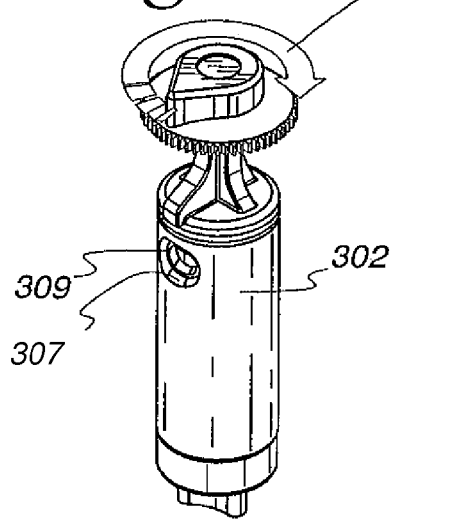
Figure 4A:
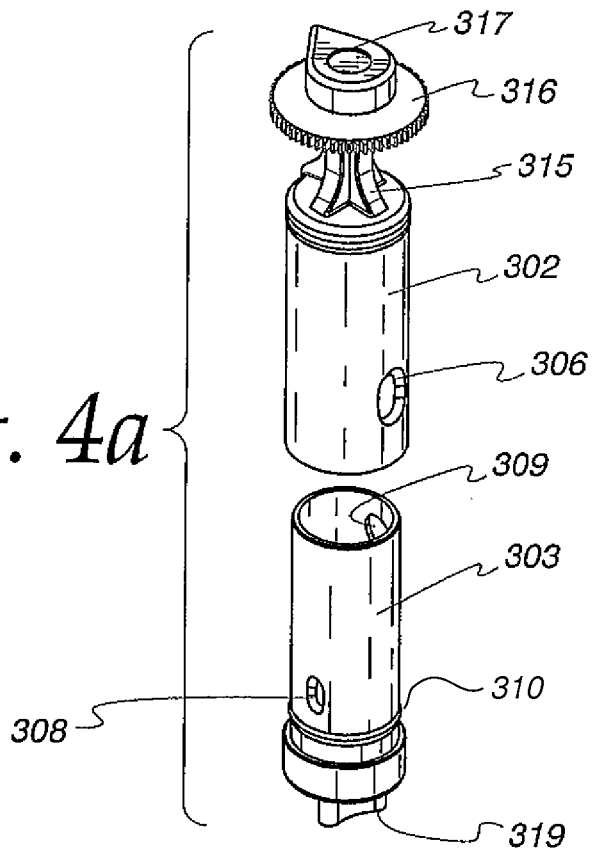
FIGS. 4a, 4b and 4c, is a rear isometric view of the medicament-containing cartridge used with the inhaler shown in FIG. 3, showing inlet hole or orifice port alignments.
Figure 4B:
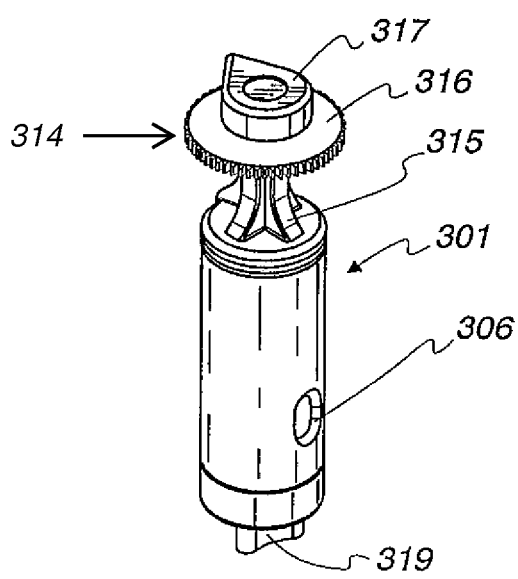
Figure 4C:
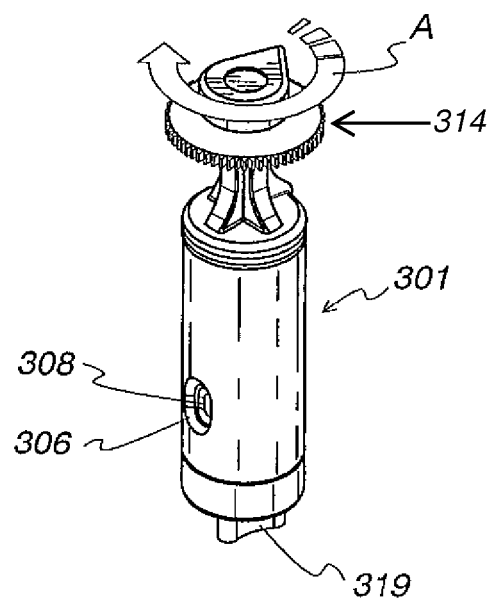
Figure 7:
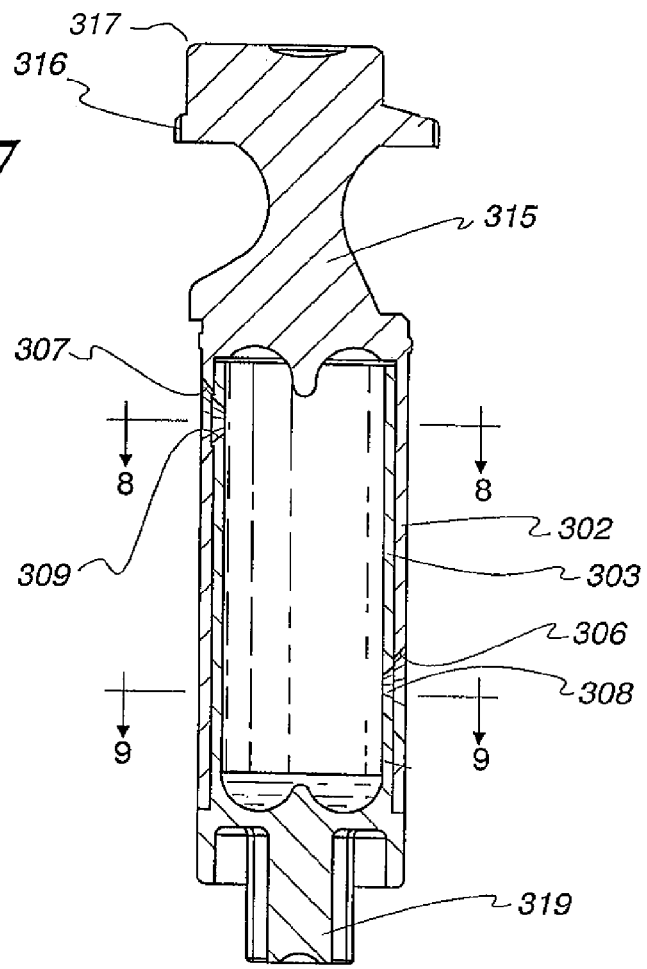
FIG. 7 is a sectional view taken substantially in the plane of line 7-7 in FIG. 5.
Figure 8:
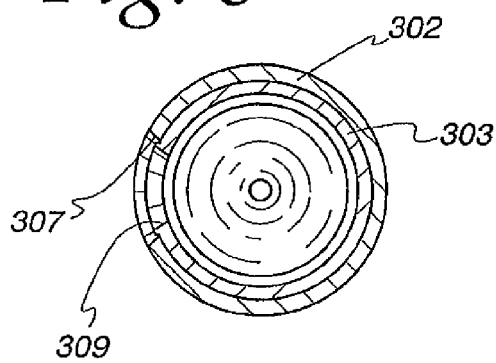
FIG. 8 is a sectional view taken substantially in the plane of line 8-8 in FIG. 7.
Figure 9:
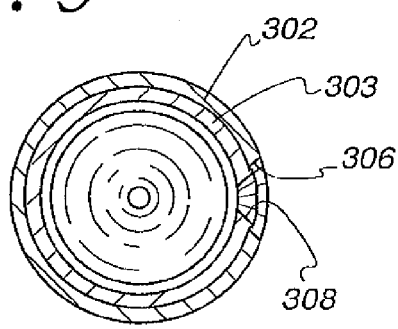
FIG. 9 is a sectional view taken substantially in the plane of line 9-9 in FIG. 7.
Figure 10:
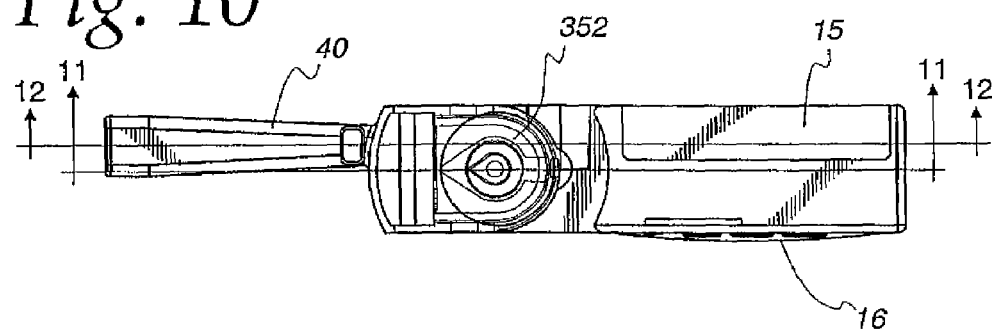
FIG. 10 is a top plan view of the inhaler shown in FIGS. 1 and 2.
Figure 11:
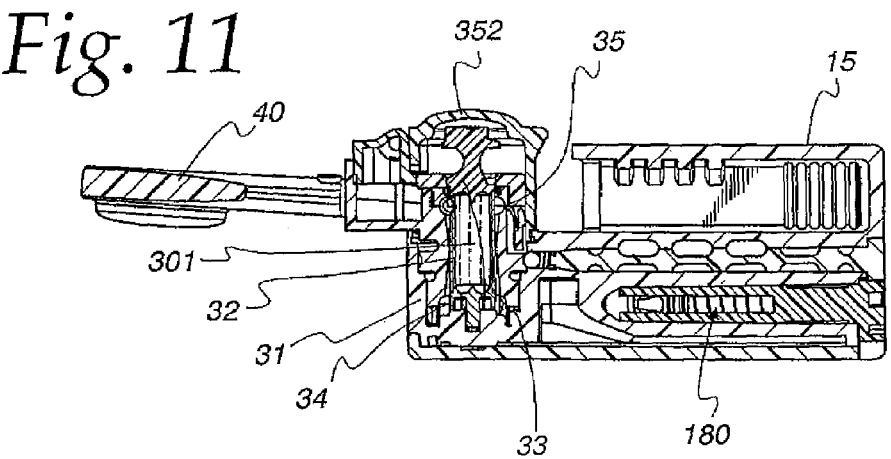
FIG. 11 is a sectional view taken substantially in the plane of line 11-11 in FIG. 10.
Figure 12:
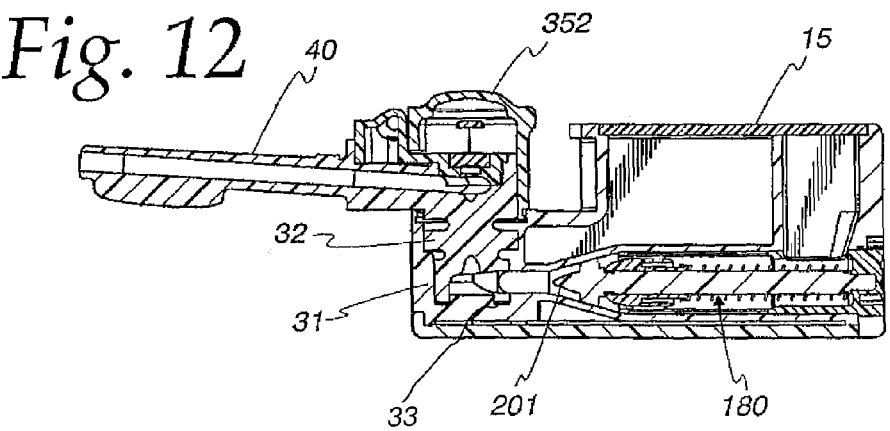
FIG. 12 is a sectional view taken substantially in the plane of line 12-12 in FIG. 10.
Figure 13:
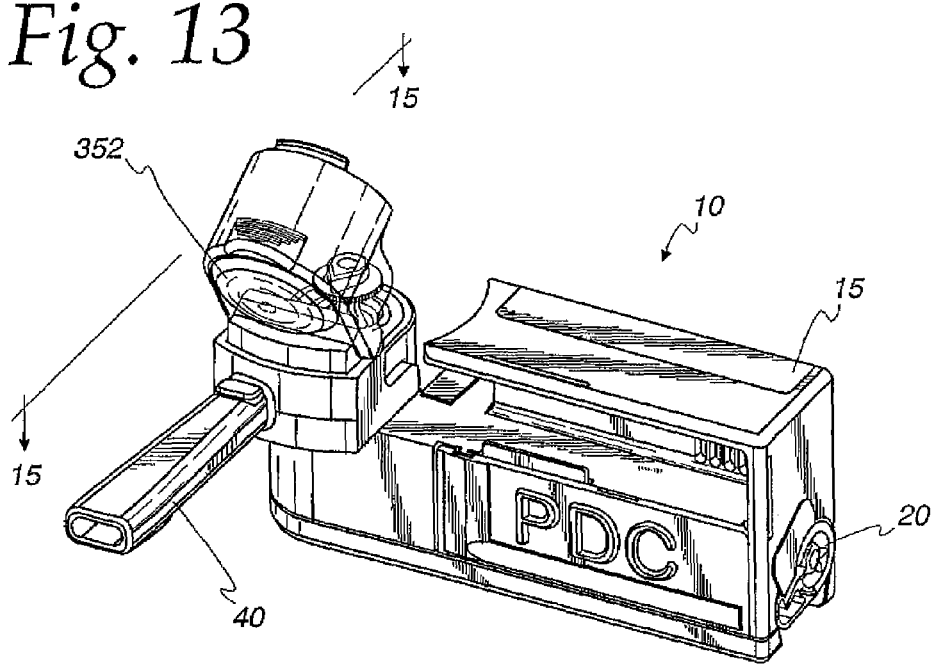
FIG. 13 is an isometric view of the inhaler shown in FIGS. 1 and 2 but configured for the insertion or removal of a medicament-containing cartridge.
Figure 14:
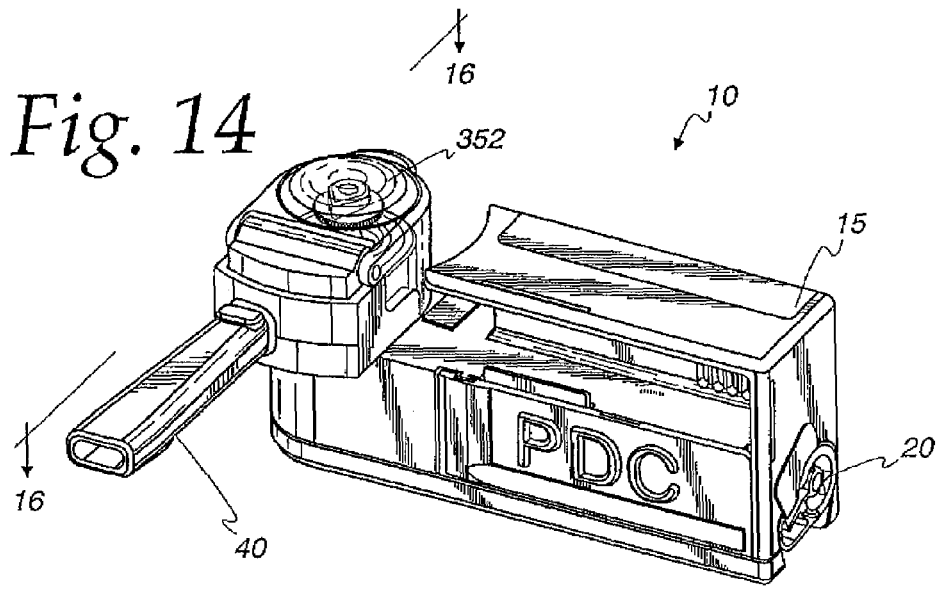
FIG. 14 is an isometric view similar to FIG. 13 but configured as it appears when a medicament-containing cartridge has been inserted in the inhaler.

An air passage 50 (FIG. 17) extends through the intake section 20, the mixing section 30 and the mouthpiece 40. A swivel joint 80 (FIGS. 2 and 17) connects the mouthpiece 40 to the mixing section 30. In the preferred embodiment, the mouthpiece and mixing section are one unit, and are connected by a swivel joint to the main housing. The cap 352 is pivotally attached to the mixing section 30, and an interlock mechanism 355 prevents the mouthpiece 40 from being swung into an operating position unless the cartridge 301 is properly seated and installed. A cartridge 301 shown in FIGS. 3, 4 and 5 contains a medicament powder, and it can be installed in and removed from the mixing chamber 30.

Figure 18:
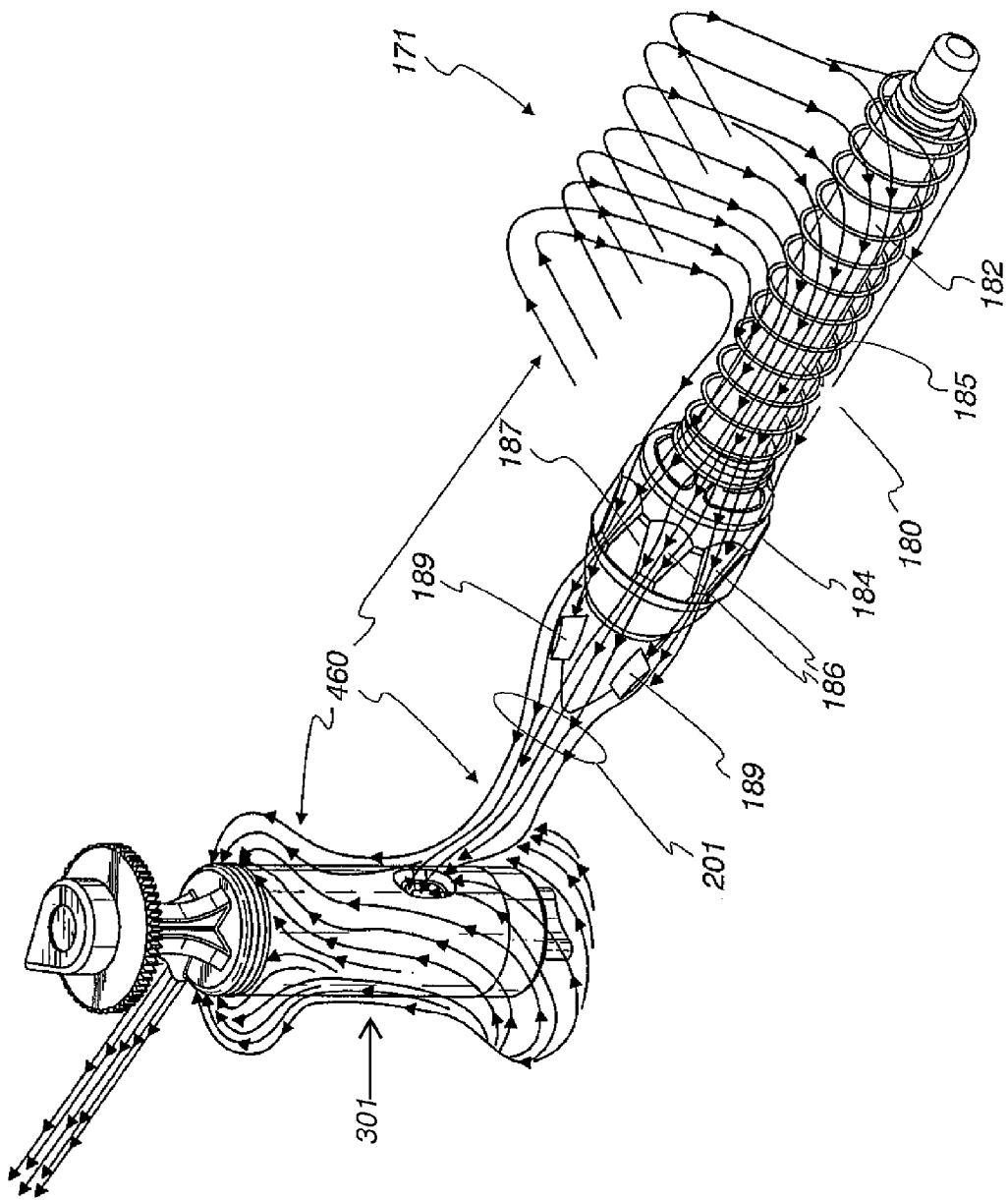
FIG. 18 is an isometric view similar to FIG. 17 diagramming air flow through and around the inhaler check valve, mixing section, cartridge and mouthpiece.
Figure 19:
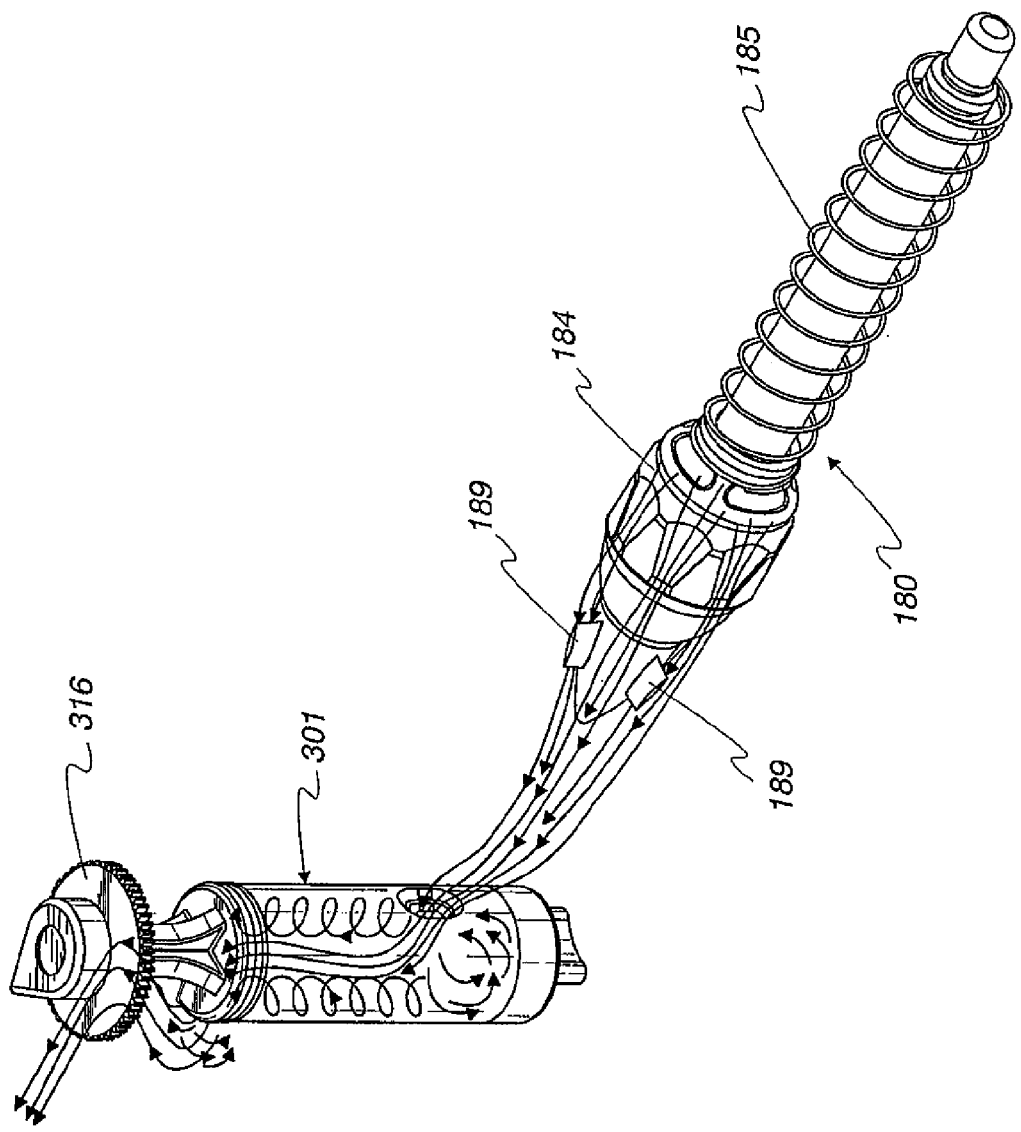
FIG. 19 is an isometric view similar to FIG. 18 diagramming air flow through and around the inhaler check valve, inside the cartridge, and through the mouthpiece.
Figure 20:
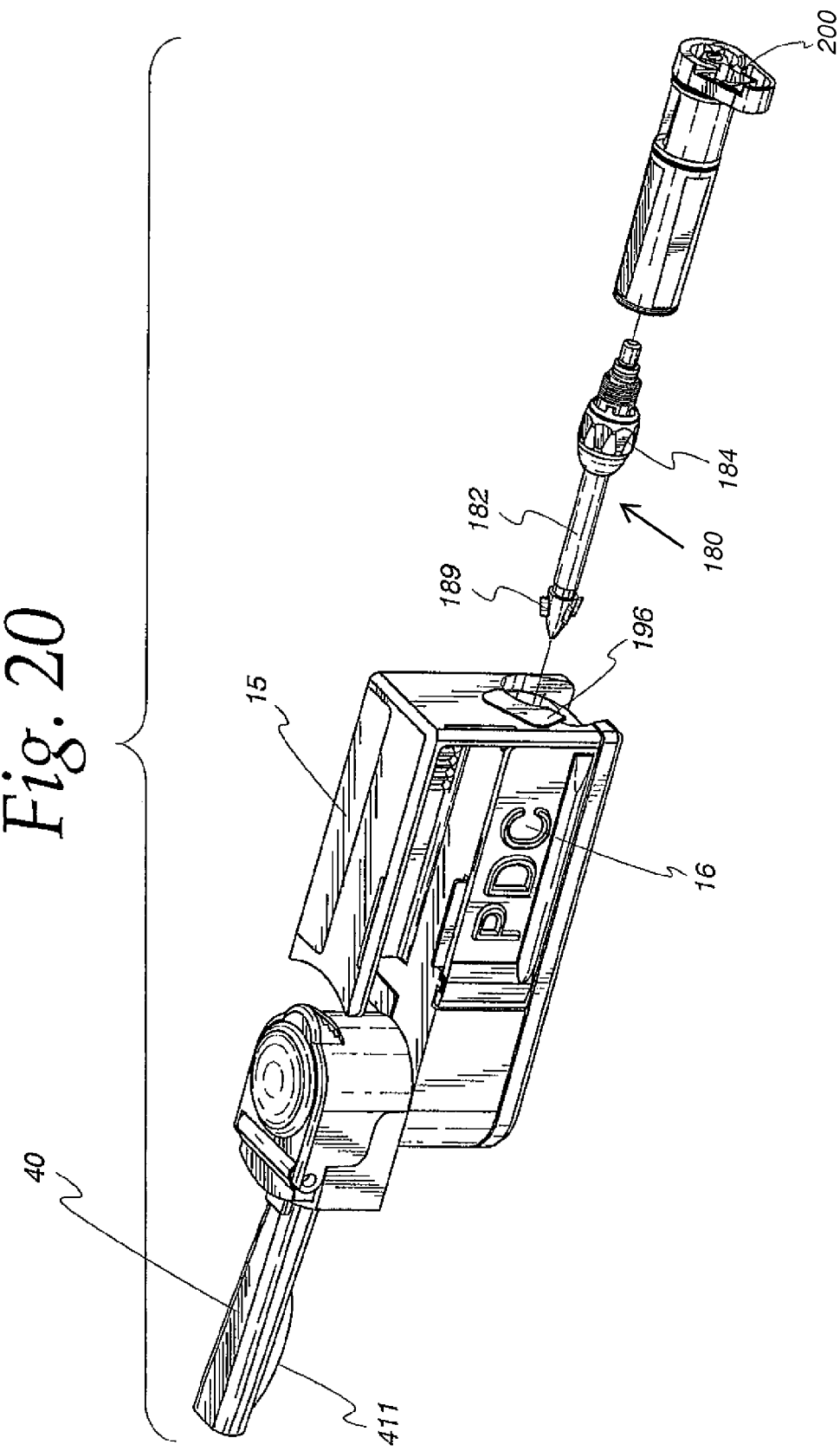
FIG. 20 is an isometric view similar to FIGS. 1, 2, 17, 18 and 19 showing the inhaler, the inhaler flow-control/check-valve, and the flow-control/check-valve sub-housing.

Aerosolized powder is drawn from the cartridge 301 and mixing section 30 through the mouthpiece 40 to the users' oropharangeal cavity via the mouthpiece 40. As air and powder travel through the mouthpiece, the velocity of the travel slows, thus preparing the powder for effective delivery to the inhaler user's broncheal tract and lungs.

So that writing or identifying indicia on medicament-containing cartridge 301 can be read easily, the mixing section 30 has a cap 352 which may be configured as a transparent magnifying lens. An arrow 460 (FIG. 17) shows the direction of aerosolized medicament powder discharge from the cartridge and through the mouthpiece.

Air is caused to enter the inhaler by an inhalation effort which the inhaler user exerts on and in the mouthpiece 40. As shown particularly in FIG. 17 and as suggested by the air-flow arrows 460 in FIGS. 17 and 18, ambient air enters the air control system 171 through air intake ports 172 and is directed to an air flow-control/check-valve 180. As shown in FIGS. 17, 18, and 25, this check valve system 180 includes a conical head 181 mounted upon a bulb rod 182. A bulb 184 is slidably mounted upon the rod 182 for reciprocation between a stagnant air-flow position and a dynamic air-flow-inhibiting position. The bulb 184 is drawn into a normal relatively downstream air-flow position, by the force of air flow acting to overcome the bulb reactive force of a conical tension spring 185 as suggested particularly in FIG. 19. This spring is preferably formed of medical grade stainless steel. Chute-like recesses 186 in the surface 187 of the bulb 184 control and direct the flow of air over the bulb 184. Air-flow straightening vanes 189 mounted on the conical head 181 engage a confronting conical venturi formation or seat 191 (FIG. 22). Air flowing between the head 181 and seat 191 is accelerated and the air-flow straightened, in accordance with known characteristics of gaseous air-flow.

When the inhaler user draws air through the mouthpiece 40, air flows to and around the bulb 184, and the imbalance of air pressure forces acting upon the reciprocating bulb 184 pushes the bulb in a downstream direction along the rod 182 into positions which inhibits air-flow. Because the bulb 184 is mounted to the tension spring 185, increasing amounts of force are required to draw the bulb 184 into increasingly air-flow-restricting positions. Additional bulb movement control can be provided, if desired, by an opposing second spring (not shown) forming a high-sensitivity push-pull system.

This bulb and spring mechanism allow the inhaler user to generate a slight partial vacuum in his lungs before the bulb is drawn away from the seating arrangement. Thus, by the time significant vacuum is generated, a slight velocity increase of air-flow through the inhaler assists in drawing the medicament from the cartridge (FIGS. 1 and 17-19), through the inhaler and into the bronchial region and lungs of the user.

As suggested particularly in FIG. 20, the check valve arrangement 180 can be mounted in a sub-housing 200 of intake section 20, and both components 20 and 180 can be removed from the inhaler housing 15 for cleaning, repair or replacement. A lock device 196 of known design can be used to secure the sub-housing 200 of intake section 20 and contained components within the inhaler housing 15.

When air is being drawn through the inhaler 10 and the bulb 184 is drawn along the rod 182 so as to impact the conical head 181, a clicking sound is produced. In accordance with one aspect of the invention, this clicking sound indicates to the inhaler user that he or she is drawing properly upon the mouthpiece and operating the inhaler correctly. If desired, a vibratory mechanical reed (not shown) can be mounted in the air-flow path to produce an audible signal to the user. Alternatively, an electronic flow or pressure sensor can trigger an audible or visual signal indicator to tell the user that proper air flow has been established.

This air flow-control/check-valve system 180 serves to deliver air at a predetermined volume and velocity to downstream inhaler parts. The air-flow, at this predetermined volume and velocity, acts to pick-up, fluidize, de-agglomerate and deliver entrained medicament particles to the inhaler user in a dispersed form and at a proper location to enter the user's bronchial system.

Venturi and Mixing Section

As suggested particularly in FIGS. 12, 17 and 18, the air flow is then drawn through a venturi passage 201 of restricted size, thus increasing the velocity of that air-flow, and into the inhaler mixing section 30. As shown in FIGS. 10-17, this mixing section 30 here comprises a fixed support 31 upon which is journaled a cup 32. It will be noted that the mouthpiece 40 is attached to the swivel cup 32 and can thus act as a handle for pivoting the cup member 32 and mouthpiece to the configurations shown in FIGS. 1, 14 and elsewhere and as more fully described below.

In general, the mixing section 30 is provided with shapes on its interior surface to encourage air flow acceleration so as to suspend medicament particles in the air-flow and to de-agglomerate them. Within the cup 32 a medicament-containing cartridge 301 can be mounted. As more frilly described below, the cartridge 301 is provided with air inlet and outlet holes (FIGS. 5-9), the cup 32 is sized and shaped to direct air into the cartridge through the lower inlet hole. The air then generally flows up through the cartridge in an upward direction while producing a dual counter-rotating helical motion, and out of the cartridge and down the mouthpiece as particularly suggested in figure 19. As suggested in FIG. 18, excess volume of air can flow Mound the outside of the cartridge but within the mixing chamber to again mate with the emerging medicament-laden air discharged from the cartridge and flowing into the mouthpiece. Thus, air flowing into the mixing chamber feeds the cartridge inlet holes, helps to extract air flowing out from the cartridge discharge holes, dilutes the medicament-laden air flow, and provides controlled, even concentrations of medicament particles into the mouthpiece air flow. The particle entrainment and dilation in the mouthpiece are provided primarily by the cartridge bypass air.

Figure 23:
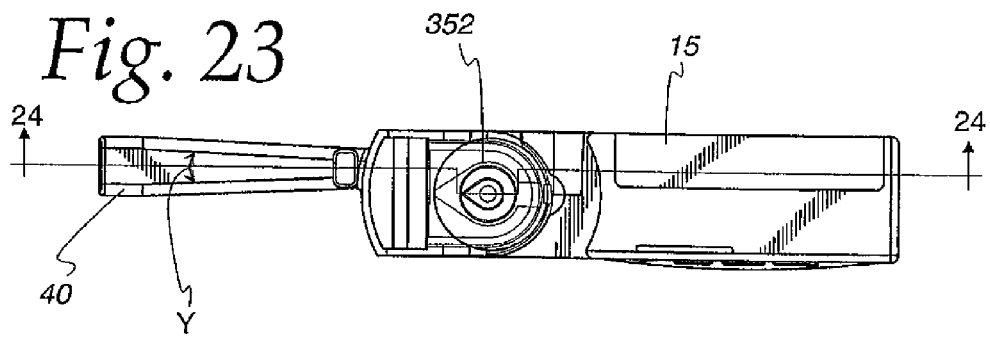
FIG. 23 is a top plan view substantially similar to FIG. 21.
Figure 24:
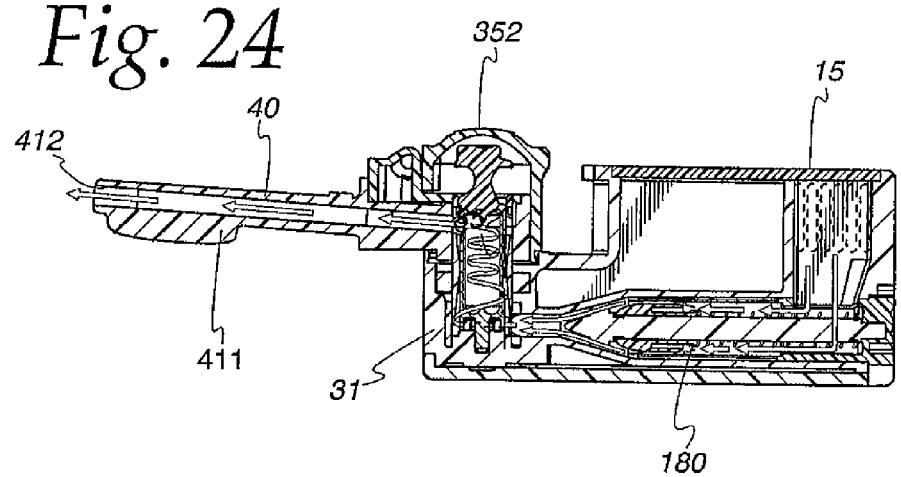
FIG. 24 is a sectional view taken substantially in the plane of line 24-24 in FIG. 23.
Figure 25:
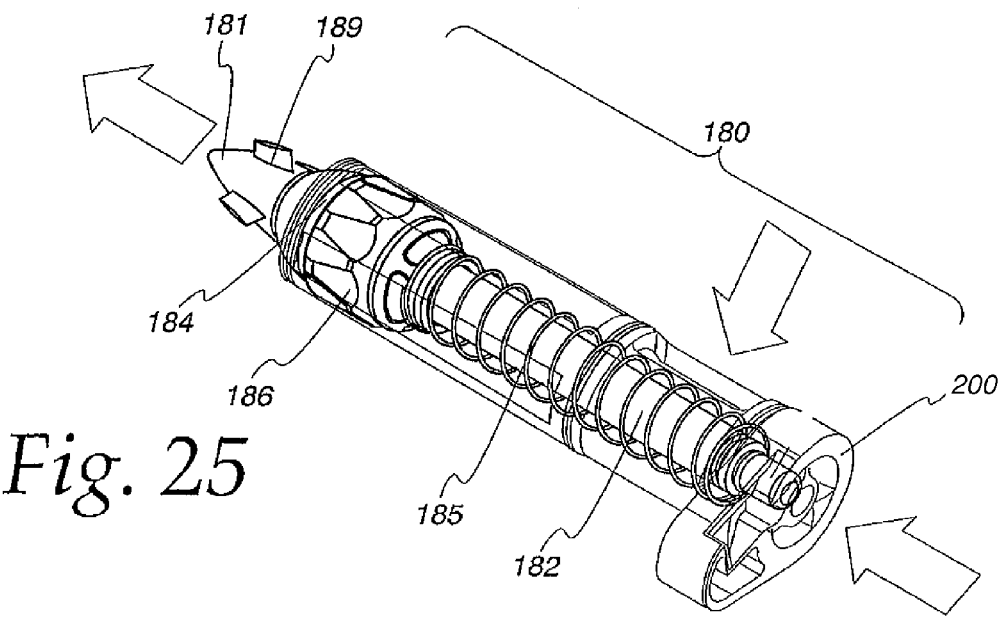
FIG. 25 is an isometric view of the flow-control/check-valve and sub-housing shown on FIGS. 17, 18, 19, 20, 22 and 24.

As suggested in FIGS. 11, 12, 15 and 16, the mixing chamber inlet port 33 provides vortex shedding which, aided by the top and bottom internal mixing chamber internal swirl toroids 34 and 35, fluidizes, suspends and scrubs the powder in the cartridge. The upper semi-toroid shape 35 changes air flow direction from dispersion chamber to mouthpiece, thus aiding further de-agglomeration of the medicament particles in the entrained powder stream. To reduce powder cohesion, a modest gas expansion velocity with subsequent air shearing forces (and flow resistance) act to support a fully dispersed flow through mouthpiece 40.

Alternatively, a chamber which includes internal protrusions or spiral shapes can be provided. The interior surfaces of the mixing chamber can be shaped to provide one or more helical flows of air around and within the cartridge, if desired.

Cartridge

The cartridge 301 is shown in further detail in FIGS. 3-9. In the illustrated embodiment, the cartridge 301 comprises an upper half 302 and a lower half 303, each preferably formed of transparent plastic material. To encourage medicament particle dispersion, the preferable plastic material is provided with ultra smooth surfaces, is capable of being molded into the cartridge components which have and which maintain great dimensional accuracy, does not absorb or otherwise interact with water or moisture, and has electrostatically neutral characteristics such that the medicament powder in the cartridge 301 is not retained by cartridge static charge, and does not adhere to the cartridge halves 302, 303. One such material which can be used for the lower half 303 is the Topaz brand of cyclicolephin co-polymer plastic offered by Ticonia Corporation.

The upper cartridge half 302 defines an air inlet hole 306 and an outlet hole 307, and the cartridge lower half defines a corresponding air inlet hole 308 and an air outlet hole 309. This upper half can be made of a clear very low water absorbent nylon. As shown particularly in FIG. 7, and as suggested in FIG. 3*a*, the halves 302 and 303 interengage through a telescopic fit. A circumferential ring and groove arrangement 310 retain the halves 302 and 303 in their assembled configuration.

As suggested particularly in FIGS. 5, 6, 8, and 9, the inlet holes 306 and 308 formed at the lower portion of the cartridge are beveled, and the outlet holes 307, 309 are likewise beveled at an angle of substantially 60 degrees so as to encourage air ingress and egress but to discourage electrostatic adhesion and agglomerate deposition of 10 or larger micron-sized medicament particles on the plastic defining the hole edges. To enable air flow and particle pickup action, the inlet holes 306 and 308 are arranged to overlap or register with one another when the cartridge halves are twisted (as suggested by the arrow A in FIG. 4*c*) into the appropriate cartridge open position, and the holes 306, 308 are elongated in a vertical direction. Similarly, the outlet holes 307, 309 are arranged to overlap and provide free air egress when the cartridge halves are appropriately aligned, and the holes are elongated in a horizontal direction so as to orient the air outflow for delivery to the horizontally elongated channel in the mouthpiece 40.

This cartridge 301 is approximately one-quarter inch in diameter and its body is approximately 1 inch in axial length, and so to facilitate easy installation and extraction from the inhaler 10, a handle or manipulator structure 314 is provided atop the cartridge 301. Here, the handle structure 314 comprises four web extensions 315 which extend from the cartridge body to a finger disk 316 which may have a coined or serrated periphery. A pointer or dial indicator 317 is formed atop the disk 316 and is further discussed below.

At the bottom of the cartridge 301, a cartridge installation check boss 319 is formed. In accordance with another aspect of the invention, this check boss can have a unique, non-circular shape of any desired form such as those shown in figures 16*a*, 16*b* and 16*c*. These unique embossments are designed to fit within a closely mating relief 39 formed in the fixed support 31 of the mixing section. These unique embossed shapes will be uniquely associated with particular medicaments, so that a cartridge containing an incorrect medicament cannot be installed in a particular patient's inhaler.

Cartridge Mounting Mechanism

To properly mount the cartridge 301 in the inhaler 10, a mounting mechanism is provided as especially shown in FIGS. 1, 2, 13-16 and 17. This mounting mechanism takes the form of a cap 352 formed of clear plastic, pivotally mounted to cover the mixing section cup 32. See especially FIG. 16. A pivot pin 353 interconnects the cap 352 with an extension 354 of the mount 31. To facilitate reading indicia marked upon the top of the cartridge pointer 317, the top of this cap 352 is curved so as to act as a magnifying lens. This dome shape also provides strength to the cover structure.

The cartridge can be installed and the cap 352 secured in place when the mouthpiece 40 and cartridge are pivoted into their operating positions. To this end, a radially outwardly biased lock pin 356 (FIG. 2) depending from the cap mount 331 pushes the cap 352 upwardly and into an open position when the mouthpiece 40 and cap mount 331 are swiveled into a position so that the mouthpiece is located at approximately 90 degrees to the long or greater dimension of the inhaler body 15. In this configuration, the lock pin 356 is pushed radially outwardly and the cap 352 is rotated upwardly when the lock pin 356 is pushed into a relief defined in a skirt 360 of the cover 358 (FIG. 2). This arrangement acts as a safety and user prompting feature.

After the cartridge is inserted into the inhaler and the cap is closed, the mouthpiece 40 can be pivoted out of its cartridge installation and cap release position as shown in FIGS. 13-16 and into the user medication inhalation configuration shown in FIGS. 1, 17 and 20-24. This mouthpiece pivoting motion can occur only when the cap skirt 360 is pushed down into its closed position and the lock pin 356 is radially depressed so as to permit mouthpiece 40 swiveling action. Thus, when the inhaler user moves the mouthpiece from its stored position within the housing 15 to the cap unlocked position, the cap springs open as shown in FIGS. 13 and 15, and thereby indicates to the inhaler user that he or she should inspect and, if necessary, replace or insert a new cartridge 301.

Mouthpiece

As suggested above, the mouthpiece 40 discharges particle-laden air to the oropharyngeal cavity of the user. In addition, the mouthpiece diverges the air and particle stream to slow down the particles, and then converges the particle stream to collimate and aim the particles at the rear of the user's mouth. The mouthpiece is long enough so that it extends approximately midway into most users' mouths. To encourage correct inhaler and mouthpiece usage, the inhaler mouthpiece is oriented so as to extend diagonally upwardly at approximately a 3 degree angle X as suggested in FIGS. 22 and 24. As suggested in FIGS. 21 and 23, the horizontally spaced walls of the mouthpiece diverge at an angle Y of approximately 5 to 8 degrees. As suggested by a comparison of FIGS. 21 and 22, the ratio of the height H of the mouthpiece air passage page to the width W of the air passage is approximately 3:1. If desired, a tooth and lip placement embossment 411 can be provided to depend from the distal end 412 of the mouthpiece 40. The mouthpiece is preferably made of Delrin or Celcon co-polymer acetyl plastic so as to provide proper strength, swivel bearing self-lubricity, and smooth internal and external finish.

In use, the inhaler employs a regulated flow of air to fluidize and aerosolize medicament particles and transport them to the desired rear region of the orophalangeal cavity. To accomplish this, air is first drawn into the interior of the inhaler housing 15 and through the intake ports 172 as suggested in FIGS. 17 and 18, to a predetermined volumetric air flow which is controlled by the flow-control/check-valve mechanism 180. The airstream then enters into the cartridge interior through the vertically elongated and aligned inlet ports 306. The air entering the cartridge interior immediately impinges upon the opposite cylindrical cartridge wall. The impacted air jet then redistributes itself into several portions. One of the portions flows downwardly into the medicament powder bed, and strips the powder from the cartridge surface and begins to fluidize it into an airborne dust cloud. Another portion of the impingement jet is directed laterally in both directions, which creates dual counter-rotating vertical spinning helical columns. The majority of the fluidized medicament powder is retained in these two columns, where the first deagglomeration action is achieved. Yet another portion of the impingement jet is directed vertically, which creates a vertical high-speed air jet along the cartridge wall into the cartridge discharge port or holes 306, 309. Particles in the helical aerosolized columns are scavenged into the jetstream and then discharged from the cartridge. This scavenging effect results in particles being metered out or discharged from the cartridge at a relatively steady particle distribution rate. Particle agglomerations are further broken down by the discharge process. Large agglomerates impinge upon the opposing mixing chamber wall, and are further reduced into smaller agglomerates. Single particles and smaller agglomerates are carried forward through the mixing chamber and into the mouthpiece discharge tube. The remaining agglomerates are pulled apart in the high-shear and shock flow field produced by the mouthpiece tangential entry port. Thus a steady flow of a individual medicament particles emerge from the mouthpiece and into the users oropharyngeal airway. These airstream flows and the sub-stream flows thus result in complete air entrainment of all medicament particles in the cartridge, and delivery of a complete, closely metered medicament dose to the patient.

We claim:

1. A medicament-dispensing inhaler comprising, in combination, a mouthpiece adapted to deliver airborne medicament to a patient's upper respiratory tract at a position away from the patient's mouth front and upper oropharyngeal region, and a housing, the housing having a mixing cavity adapted to selectively mount a medicament-containing cartridge; and an air-flow cavity for assisting in the delivery of air into and through a cartridge in the mixing cavity and into and through the mouthpiece, further including a cartridge comprising a first element defining an air inlet hole and an air outlet hole, and a second element, the second element snugly fitted into the first element so as to define, with the first element, a medicament-containing cavity, the second element also defining an air inlet hole and an air outlet hole, the first element and the second element being movable with respect to one another so as to place the air inlet holes in the first element and the second element in registry with one another and to simultaneously place the air outlet holes in the first element and the second element in registry with one another so as to permit a flow of air into, through, and out of the cartridge, the first element and the second element being movable with respect to one another so as to reconfigure the first and second elements thereby placing the inlet and outlet holes out of registry with one another and thereby prohibiting air flow through the cartridge and securely retaining medicament within the cartridge.

2. An inhaler according to claim 1 wherein said mixing cavity includes cartridge mounting mechanism adapted to mate only with a three-dimensional cartridge structure of a pre-determined shape.

3. An inhaler according to claim 1 wherein said mouthpiece comprises a hollow tube having an axis, and wherein said mixing chamber comprises a hollow cylinder having an axis, and wherein the angle defined by the mouthpiece axis and the mixing chamber axis is between about 93 degrees and about 120 degrees.

4. An inhaler according to claim 1 further including mechanism for generating a signal in response to air flow through the inhaler.

5. An inhaler according to claim 1 wherein the mouthpiece has an outer surface and a protrusion on the outer surface adapted to contact the teeth and lip of the user so as to indicate to the user that the inhaler has been inserted into the oral cavity of the user in a correct position.

6. An inhaler according to claim 1 wherein an opening of the mouthpiece to be inserted into the mouth of a user has a major axis and a minor axis, and wherein the horizontal aspect ratio of these axes is between 2:1 and 4:1.

7. An inhaler according to claim 6 wherein said horizontal aspect ratio of the axes is substantially 3:1.

8. A medicament-dispensing inhaler, comprising, in combination, a mouthpiece adapted to deliver airborne medicament to a patient's upper respiratory tract at a position away from the patient's mouth front and upper oropharyngeal region, and a housing, the housing having a mixing cavity adapted to selectively mount a medicament-containing cartridge; and an air-flow cavity for assisting in the delivery of air into and through a cartridge in the mixing cavity and into and through the mouthpiece, and a cartridge mounted within the mixing cavity, the cartridge comprising a first element defining and air inlet hole and an air outlet hole, a second element snugly fitted to the first element so as to define, with the first element, a medicament-containing cavity, the second element further defining and air inlet hole and air outlet hole, the first element and the second element being movable with respect to one another so as to place the air inlet holes in the first element and the second element in registry with one another and to simultaneously place the air outlet holes in the first element and the second element in registry with one another so as to permit a flow of air into, through and out of the cartridge; the first element and the second element being movable with respect to one another so as to reconfigure the first and second elements to thereby place the element inlet and outlet holes out of registry with one another and thereby prohibit air flow through the cartridge and securely retain medicament within the cartridge.

9. An inhaler according to claim 8 wherein said first and second cartridge elements have a substantially circular cross-sectional aspect and wherein said first and second elements are fitted together with an at least partially overlapping telescopic fit so as to permit said first and second elements to be angularly twisted, relative to one another, between said configurations.

10. An inhaler according to claim 8 wherein at least some of said cartridge element inlet holes and outlet holes are defined by a beveled cross-sectional shape.

11. An inhaler according to claim 8 wherein said cartridge first element and second element are interlocked by ring and groove seals.

12. A medicament-dispensing inhaler, comprising, in combination a mouthpiece adapted to deliver airborne medicament to a patient's upper respiratory tract at a position away from the patient's mouth front and upper oropharyngeal region, and a housing, the housing having a mixing cavity adapted to selectively mount a medicament-containing cartridge and air-flow cavity for assisting in the delivery of air into and through a cartridge in the mixing cavity and into and through the mouthpiece, and a cartridge mounted within the mixing cavity, the cartridge comprising a hollow first element defining an air inlet hole and an air outlet hole, a hollow second element snugly fitted to the first element so as to define, with the first element, a medicament-containing cavity, the second element further defining an air inlet hole and an air outlet hole, the first element and the second element being twistable with respect to one another so as to place the air inlet holes in the first element and the second element in registry with one another and to simultaneously place the air outlet holes in the first element and the second element in registry with one another so as to permit a flow of air into, through, and out of the cartridge; the first element and the second element being movable with respect to one another so as to reconfigure the first and second elements to thereby place the element inlet and outlet holes out of registry with one another and thereby prohibit air flow through the cartridge and securely retain medicament within the cartridge, the inhaler further comprising a swivel mechanism for twisting the mouthpiece between a storage position, a cartridge insertion and removal position, and a use position; and for simultaneously twisting the cartridge first and second elements between an air-flow-permitting configuration and a medicament-retaining configuration.

13. An inhaler according to claim 1 wherein said cartridge elements are made of a transparent plastic having neutral electrostatic characteristics.

14. A medicament-dispensing inhaler comprising, in combination, a mouthpiece adapted to deliver airborne medicament to a patient's upper respiratory tract at a position away from the patient's mouth front and upper oropharyngeal region, and a housing, the housing having a mixing cavity adapted to selectively mount a medicament-containing cartridge; and an air-flow cavity for assisting in the delivery of air into and through a cartridge in the mixing cavity and into and through the mouthpiece, further including an air-flow controlling check valve mechanism adapted to be mounted within the housing air-flow cavity for assisting in the delivery of an air-flow of predetermined velocity and volume into and through the cartridge and mouthpiece wherein said air-flow-controlling check valve mechanism includes an air passage bore of extended length for straightening air-flow, a bulb reciprocable in said bore, and biasing means urging said bulb out of an air-flow inhibiting position.

15. An inhaler according to claim 14 wherein said check valve mechanism includes a rod upon which said bulb can reciprocably travel; and a rod head having vanes mounted thereon, said vanes engaging a venturi passage.

16. An inhaler according to claim 14 wherein said biasing means comprises a spring positioned and connected to said bulb with a tensile force to urge said bulb out of an air-flow in inhibiting position.

17. An inhaler according to claim 14 wherein said spring has a spring rate selected so as to let said bulb to be drawn away from its air-flow-inhibiting position only when the air-flow across and past said bulb creates a force sufficient to provide an air-flow of a volume and rate sufficient to cause said air-flow to take up medicament in the cartridge, de-agglomerate the fluidized medicament and deliver the medicament to the user's upper respiratory tract in a dispersed form.

18. An inhaler according to claim 14 further including a rod mounted in said air flow passage, and vanes mounted on said rod to straighten air-flow passing said vanes, and to center and align the rod within the inhaler housing receiving bore.

19. An inhaler according to claim 14 further including a check valve subhousing removably mountable in said inhaler housing, the subhousing mounting said bulb and said biasing means.

20. An inhaler according to claim 1 wherein said first and second cartridge elements have a substantially circular cross-sectional aspect and wherein said first and second elements are fitted together with an at least partially overlapping telescopic fit so as to permit said first and second elements to be angularly twisted, relative to one another, between said configurations.

21. An inhaler according to claim 1 wherein said at least some of said cartridge element inlet holes and outlet holes are defined by a beveled cross-sectional shape.

22. An inhaler according to claim 1 wherein said cartridge first element and second element are interlocked by ring and groove seals.

23. An inhaler according to claim 1 wherein said cartridge elements are made of a transparent plastic having neutral electrostatic characteristics.

24. An air-flow controlling check valve mechanism adapted to be mounted within a housing air-flow cavity of an inhaler for assisting in the delivery of an air-flow of predetermined velocity and volume into and through an inhaler cartridge and mouthpiece wherein said check valve mechanism includes an air passage bore of extended length for straightening air-flow, a bulb reciprocable in said bore, and a venturi communicating with said bore.

25. An air-flow controlling check valve mechanism according to claim 24 further including a rod mounted in said bore, said bulb being mounted on said rod for reciprocable motion.

26. An air-flow controlling check valve mechanism according to claim 24 wherein said biasing means comprises a spring positioned and connected to said bulb with a tensile force to draw said bulb away from said venturi.

27. An air-flow controlling check valve mechanism according to claim 26 wherein said spring has a spring rate selected so as to permit said bulb to be drawn away toward said venturi only when the air-flow across and past said bulb creates a force to provide an air-flow of a volume and rate to cause said air-flow to take up medicament in the cartridge, de-agglomerate the fluidized medicament and deliver the medicament to the user's upper respiratory tract in a dispersed form.

28. An air-flow controlling check valve mechanism according to claim 24 further including chutes mounted on the perimeter of said bulb to straighten air-flow passing over and around said bulb.

29. An air-flow controlling check valve mechanism according to claim 24 further including a check valve subhousing removably mountable in said bore, the subhousing mounting said bulb, and said biasing means.

30. A method of using an inhaler to deliver a pre-determined amount of medicament to an inhaler user, comprising the steps of installing a cartridge containing the predetermined amount of medicament in the inhaler, configuring the cartridge for medicament delivery by configuring the inhaler for use, and drawing a predetermined volume of air at a predetermined rate through the inhaler so as to aerosolize substantially all the medicament in the cartridge and deliver the aerosolized medicament to the user wherein said cartridge comprises at least two cartridge elements, and wherein the step of configuring the cartridge for medicament delivery comprises the step of twisting the cartridge elements relative to one another.

31. A method of using an inhaler according to claim 30 wherein the step of drawing a predetermined volume of air at a predetermined rate comprises the step of drawing air past a flow-control check valve.

32. A medicament-dispensing inhaler comprising, in combination, a mouthpiece adapted to deliver airborne medicament to a patient's upper respiratory tract at a position away from the patient's mouth front and upper oropharyngeal region, and a housing, the housing having a mixing cavity adapted to encourage a flow of air to mix with, deagglomerate and transport medicament to and through the mouthpiece wherein the inhaler includes a venturi for the regulation of proper volumetric aerosolizing air-flow through the cartridge and bypass-air-flow around the cartridge.

33. An inhaler according to claim 32 further including a cartridge adapted to contain a medicament; adapted to be mounted within the housing mixing cavity; and adapted to be altered in configuration between an open medicament-dispensing configuration and a closed medicament-retaining configuration.

34. An inhaler according to claim 32 further including an air-flow controlling check valve mechanism adapted to be mounted within the inhaler for assisting in the delivery of an air flow of predetermined velocity and volume into and through the mixing cavity.

35. A medicament-dispensing inhaler, comprising, in combination, a mouthpiece adapted to deliver airborne medicament to a patient's upper respiratory tract at a position away from the patient's mouth front and upper oropharyngeal region, and a housing, the housing having a mixing cavity including a cartridge-mounting mechanism to selectively mount a medicament-containing cartridge; the cartridge-mounting mechanism having keying structure adapted to mate uniquely with cartridge keying structures so as to permit only preselected cartridge to be mounted in and used with the inhaler wherein said cartridge-mounting mechanism includes a cap movable between an open position for mounting and de-mounting the cartridge, and a closed position permitting the inhaler to be used.

36. An inhaler according to claim 35 further including an interlock mechanism for prohibiting said inhaler mouthpiece from being used unless said cap is in its closed position.

* * * * *

UNITED STATES PATENT AND TRADEMARK OFFICE
CERTIFICATE OF CORRECTION

PATENT NO. : 7,464,706 B2  Page 1 of 1
APPLICATION NO. : 10/655153
DATED : December 16, 2008
INVENTOR(S) : Solomon S. Steiner et al.

It is certified that error appears in the above-identified patent and that said Letters Patent is hereby corrected as shown below:

Column 6, line 61, "frilly" should read --fully--.

Column 7, line 2, "Mound" should read --around--.

Column 7, line 10, "dilation" should read --dilution--.

In the claims,

Column 10, line 36, for claim 5, "lip" should read --lips-- and "the user" should read --a user--.

Column 10, line 55, for claim 8, "and air" should read --an air--.

Column 10, line 58, for claim 8, "and air inlet hole and air outlet hole" should read --an air inlet hole and an air outlet hole--.

Column 11, line 50, for claim 13, "1" should be changed to --8--.

Column 14, line 24, for claim 35, "only preselected" should read --only a preselected--.

Signed and Sealed this

Nineteenth Day of May, 2009

JOHN DOLL
*Acting Director of the United States Patent and Trademark Office*